United States Patent [19]

Phan et al.

[11] Patent Number: 5,336,380
[45] Date of Patent: Aug. 9, 1994

[54] METHOD OF MONITORING MAJOR CONSTITUENTS IN PLATING BATHS

[75] Inventors: Nguyet H. Phan, Los Angeles; Vilambi N. R. K. Reddy, Lakewood; Frank A. Ludwig, Rancho Palos Verdes; Bruce M. Eliash, Los Angeles, all of Calif.

[73] Assignee: Hughes Aircraft Company, Los Angeles, Calif.

[21] Appl. No.: 37,158

[22] Filed: Mar. 25, 1993

[51] Int. Cl.$^5$ ............................................. G01N 27/26
[52] U.S. Cl. .................................. 204/153.1; 204/434
[58] Field of Search ............ 204/402, 412, 434, 153.1; 205/81, 101, 102, 103, 104, 105

[56] References Cited

U.S. PATENT DOCUMENTS 4,631,116 12/1986 Ludwig .............................. 204/434

*Primary Examiner*—John Niebling
*Assistant Examiner*—Bruce F. Bell
*Attorney, Agent, or Firm*—M. E. Lachman; M. W. Sales; W. K. Denson-Low

[57] ABSTRACT

A method of monitoring major constituents within a plating bath. The method involves applying an electrical signal to a working electrode positioned within the plating bath solution, varying signal parameters, and measuring the resultant response signal. The characteristics of the response signal indicate major constituent concentration levels. The method complements and is easily integrated with known voltammetric techniques for analysis of trace constituents, thus forming an integral part of an efficient overall plating bath analysis system. By adjusting major constituent concentration levels in accordance with measurements made using the method of the present invention, a high quality plating bath can be easily and inexpensively maintained.

15 Claims, 9 Drawing Sheets

METHOD OF MONITORING MAJOR CONSTITUENTS IN PLATING BATHS

BACKGROUND OF THE INVENTION

1. Field of the Invention

The present invention relates generally to plating baths and methods for monitoring the major constituents contained therein. More particularly, the method of the present invention relates to a voltammetric analysis technique that provides signal spectra which accurately indicate concentrations of major constituents within the bath. The signal spectra can be used to maintain desired major constituent concentrations within limits in order to ensure optimal plating bath performance.

2. Description of Related Art

A typical plating bath solution is comprised of a combination of several different chemical constituents. The specific constituents vary depending upon the type of plating bath, but in general can be broadly divided into what are commonly known as major constituents and trace, or minor, constituents. The major constituents are defined as those chemical constituents which are in excess of 5 percent of the total bath volume. Trace or minor constituents, on the other hand, are defined as those present in smaller quantities, i.e. less than 5 percent of the total volume. For example, in an acid copper plating bath, a major constituent is sulfuric acid, which typically represents about 8 to 12 percent of the total volume. The acid copper plating bath might also contain trace constituents such as organic addition agents, degradation products and chemical contaminants, present in much smaller concentrations.

The concentration levels of both major and trace constituents are important determinants of the quality of the resultant plating deposit. Trace constituent concentrations influence certain characteristics of the plating deposit, including tensile strength, ductility, solderability, uniformity, brightness and resistance to thermal shock. Monitoring and optimization of trace constituents assumes that the major constituent concentrations within the bath are already properly set and maintained. Should the major constituents fall outside of required concentration ranges, however, the bath may fail to satisfactorily perform its plating function. It is therefore important that major constituent concentrations be regularly monitored.

Current techniques for monitoring the major constituents of plating baths typically involve removing a sample of the chemical solution from the plating tank for subsequent wet chemical analysis. Methods of measuring major constituent content in various types of plating baths are disclosed, for example, in K. E. Langford and J. E. Parker, "Analysis of Electroplating and Related Solutions", pp. 83–100, 65–68 and 174–180. In these analysis methods, for example, sulfuric acid content within an acid copper plating bath is determined using titration with sodium hydroxide; chromic acid content within a chromium plating bath is found using reduction titration with excess ferrous ammonium sulfate; free cyanide within a silver-cyanide plating bath is found by titration with silver nitrate; and carbonate within a silver-cyanide plating bath is analyzed by precipitation with barium chloride followed by titration with HCl. Major constituent concentrations in other types of plating baths are measured in a similar manner.

Wet chemical analysis methods such as the above must be performed by highly skilled personnel. Specialized and costly chemical analysis equipment and supplies are required. Furthermore, the delay between drawing samples and receiving measurement results can be anywhere from several hours to several days. It is thus very tedious and expensive to monitor major constituent concentrations using currently available techniques. Moreover, the slow response time of wet chemical analysis limits the extent to which a high quality and high speed plating bath can be continuously maintained.

The current major constituent monitoring techniques are quite different from real time trace constituent monitoring techniques such as those described in U.S. Pat. No. 4,631,116, assigned to the present assignee. The method disclosed therein uses voltammetric techniques to produce ac current spectra which vary as a result of changes in the concentration of various trace constituents. Voltammetric methods have been found to produce accurate results in real time for trace constituent analysis. However, voltammetric methods have not yet been considered for use in major constituent analysis. As a result, it is presently necessary to use voltammetric trace constituent measurement techniques in conjunction with the above-described major constituent wet chemical analysis in order to monitor the overall chemistry of the plating bath. The wet chemical analysis cannot be performed with the in-tank electrochemical sensors and other equipment typically used in trace constituent analysis. Two different sets of equipment must therefore be maintained in order to perform major and trace constituent analysis. No integrated measurement system is available which is capable of measuring both major and trace constituents.

As is apparent from the above, there presently is a need for an accurate and inexpensive real time method for monitoring the concentration of major constituents within a plating bath. Furthermore, the method should complement and be easily integrated with known techniques and equipment suitable for measuring trace constituents, resulting in an efficient overall plating bath analysis system.

SUMMARY OF THE INVENTION

In accordance with the present invention a method for monitoring the concentration of major constituents within a plating bath is provided. The present invention is based upon the discovery that voltammetric techniques can be used to accurately monitor major constituent concentrations within a plating bath. Voltammetric techniques have been used for monitoring levels of very low concentration trace constituents, but have heretofore not been considered for measuring major constituents. The method of the present invention now makes possible the use of voltammetry to accurately determine major constituent concentrations.

The method of the present invention involves the steps of applying an electrical signal to a working electrode in contact with the plating bath solution, varying the parameters of the electrical signal, and measuring the response signal. The characteristics of the response signal vary in accordance with the major constituent concentration within the solution, and thereby provide an accurate real time indication of major constituent concentration.

In accordance with a preferred embodiment of the present invention, an ac signal superimposed on a dc sweep signal is applied to a working electrode which has been pretreated by a dc potential and is in contact with the plating bath solution. The dc sweep signal is varied at a selected sweep rate over a selected voltage range. An ac response current signal is thereby produced which includes peaks indicative of the concentration levels of major constituents within the plating bath. Various independent electrochemical parameters are varied to maximize the sensitivity of the ac current spectra peaks to particular major constituents. The method establishes a set of optimal electrochemical parameters for several exemplary plating baths and their respective major constituents.

As a feature of the present invention, the method eliminates the delay, expense and complexity typically associated with current major constituent analysis methods requiring wet chemical analysis. Specialized chemical equipment and chemical analysis personnel are no longer required. The measurement results are available in real time, which facilitates continuous and efficient control of plating bath chemistry.

As another feature of the present invention, the ac response current includes a readily identifiable peak, the amplitude of which varies with the concentration of the major constituent being measured. The constituent levels within the bath can then be adjusted until the desired optimal concentrations are present.

As a further feature of the present invention, the method is easily integrated with known trace constituent measurement methods and equipment, thereby providing an efficient overall plating bath analysis system suitable for monitoring both trace and major constituents. For example, the method may be used in conjunction with an in-tank electrochemical sensor so as to eliminate the need to draw a sample of electrochemical solution from the plating bath.

As an additional feature of present invention, optimal signal parameters for monitoring the concentrations of major constituents within commonly used acid copper, chromium and silver-cyanide plating baths are provided. Furthermore, the method provides an experimental framework for determining optimal measurement signal parameters for monitoring major constituents in other types of plating baths.

The above-discussed features and attendant advantages of the present invention will become better understood by reference to the following detailed description of the preferred embodiment and the accompanying drawings.

DETAILED DESCRIPTION OF THE PREFERRED EMBODIMENT

The present invention is based upon the discovery that a known voltammetric technique, heretofore considered applicable only to the measurement of trace constituents, can be used to monitor major constituents within a plating bath. Although the following detailed description discusses only one exemplary voltammetric technique, it should be understood that the method of the present invention can be readily adapted for use with other voltammetric techniques. The exemplary voltammetric trace constituent monitoring technique to which the method of the present invention is related is described in U.S. Pat. No. 4,631,116. The contents of this patent are hereby expressly incorporated by reference.

As discussed above, major constituents within a plating bath vary depending upon the type of bath, but in general are defined as those constituents which make up in excess of 5 percent of the total plating bath volume. The following detailed description will be directed to exemplary major constituents found within the commonly used acid copper, chromium and silver-cyanide plating baths. For example, in an acid copper plating bath, one exemplary major constituent is sulfuric acid, which has a concentration of about 8 to 12 percent of total volume. In a chromium plating bath, one exemplary major constituent is chromic acid, which has a concentration of about 225 g/l to 275 g/l $CrO_3$. In a silver-cyanide plating bath, two exemplary major constituents are potassium cyanide and potassium carbonate, with typical concentrations of about 82 g/l to 113 g/l and about 40 g/l to 180 g/l, respectively. Although the following description is directed to these three exemplary plating baths and four exemplary major constituents associated therewith, it should be understood that this is by way of illustration and not limitation. The method can be used to monitor other major constituents within acid copper, chromium and silver-cyanide plating baths. Furthermore, the method discloses general techniques which are useful for monitoring many other types of plating baths and the major constituents contained therein.

Figure 1:
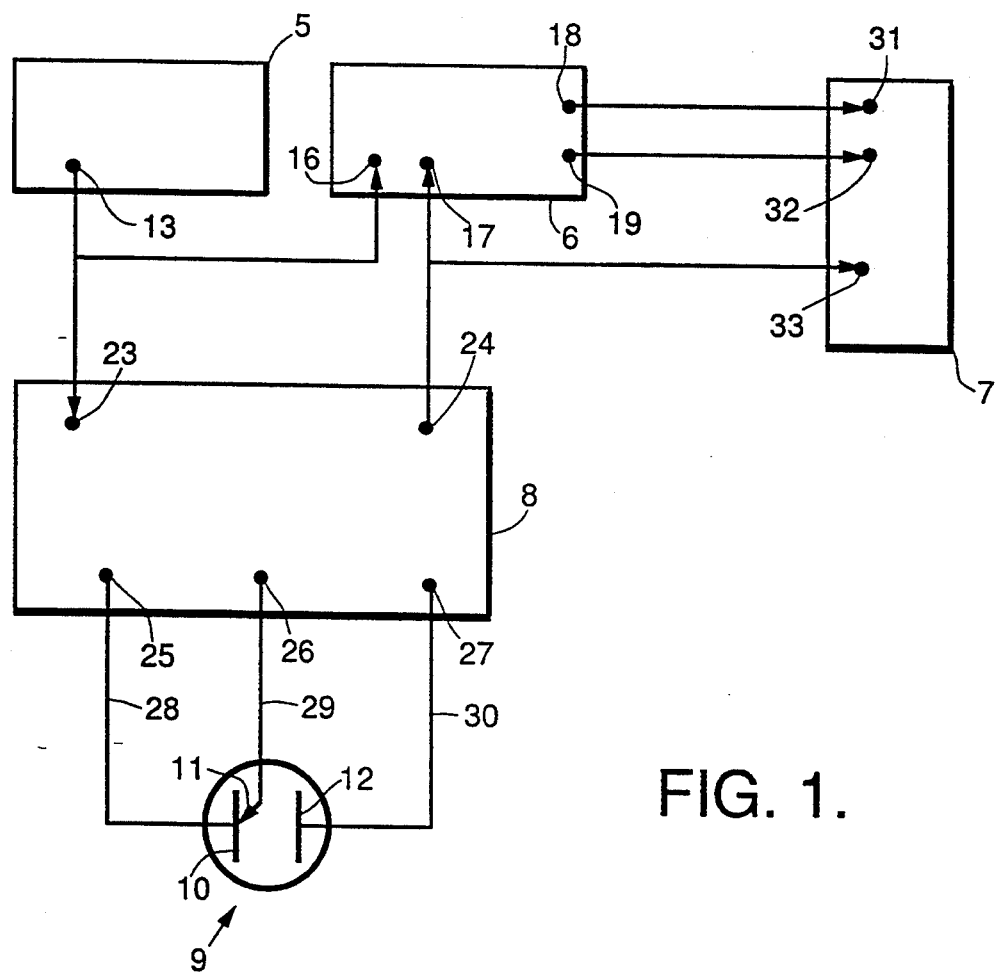
FIG. 1 is a schematic representation of a preferred embodiment of the voltammetric system used for conducting the method in accordance with the present invention.

The schematic diagram of FIG. 1 illustrates a preferred embodiment of a voltammetric system used to conduct the method of the present invention. The plating bath solution is located within an electrochemical cell 9. The electrochemical cell 9 is preferably part of an electrochemical sensor submerged within the plating bath. A pump can then be used to draw the solution through the cell. This eliminates the need to remove a sample of the solution from the tank, as is currently required by wet chemical analysis techniques.

In the exemplary system of FIG. 1, a function or waveform generator 5 provides an output 13 which is an ac signal of appropriate frequency and amplitude. The ac signal is applied to the external input 23 of a potentiostat 8 and to the reference input 16 of a lock-in amplifier 6. The potentiostat serves to superimpose the ac signal applied to its external input 23 upon an appropriate dc voltage sweep signal generated within the potentiostat. Alternatively, the dc sweep signal could be supplied by an external function generator. In some cases, the voltammetric signal is simply the one generated within potentiostat 8, upon which the AC is superimposed.

The combined dc and ac signal output from potentiostat port 25 is then applied to the working electrode 10 in the electrochemical cell 9 via line 28. The electrochemical cell 9 also contains a counter electrode 12 and a suitable reference electrode. The reference electrode 11 and counter electrode 12 are connected to the accompanying potentiostat ports 26, 27 via lines 29, 30, respectively. The electrochemical cell 9 with electrodes 10, 11 and 12 is a sensor design typically used in conjunction with voltammetric techniques. Other sensor designs could also be used. When the combined dc and ac signal is applied to the working electrode 10, a response current is generated between the working electrode 10 and the counter electrode 12. The response current is a combined dc and ac signal which varies depending upon the electrochemical processes occurring at the surface of the working electrode 10. The electrochemical processes are a function of the major constituent concentrations, and the response current is therefore responsive to these concentrations.

From the potentiostat output 24 the response current is applied to the signal input 17 of lock-in amplifier 6 and to the external sweep input 33 of strip chart recorder 7 or to a computerized data acquisition system. The lock-in amplifier filters out the DC component in the response signal and isolates out the desired harmonic component in the AC signal. It further resolves the AC harmonic signal into its in-phase and quadrature components. The ac harmonic which provides the best diagnostic information is the one which should be selected for measurement. In the exemplary spectra shown in FIGS. 2 through 9 the second harmonic of the ac portion of the response signal provided the best diagnostic information indicative of major constituent concentrations. For other plating baths or major constituents, different harmonics of the ac portion of the response signal may provide better results.

The in-phase component of the ac portion of the response current is then passed from in-phase output 18 of lock-in amplifier 6 to a display signal input 31 of strip chart recorder 7. Similarly, the quadrature component is passed from quadrature output 19 of lock-in amplifier 6 to a second display signal input 32 of strip chart recorder 7. The strip chart recorder displays the in-phase and the quadrature components of the ac portion of the response current as a function of time as shown in FIGS. 2 through 9. These displays represent unique AC response current spectra which indicate the major constituent composition within the plating bath solution.

The specific equipment used in the exemplary system of FIG. 1 included a Wavetek Model 188 waveform generator, a PAR 273 potentiostat, and a PAR 5208 (or 5210) lock-in amplifier. The Wavetek waveform generator is available from Wavetek San Diego, Inc., of San Diego, Calif. and the PAR equipment is available from Princeton Applied Research, of Princeton, N.J.

In order to optimize the accuracy of the response current spectra produced in accordance with the preferred voltammetric technique described above, it is necessary to vary a number of independent electrochemical parameters. These parameters include: 1) dc pretreatment voltage and time; 2) type of ac waveform (i.e., sinusoidal, square, triangular, etc.); 3) ac signal amplitude and frequency; 4) dc sweep signal voltage range and sweep rate; 5) ac response signal harmonic measured (i.e., fundamental, second, etc.); 6) ac response signal phase angle measured; and 7) hydrodynamic conditions (i.e., degree of agitation). The above parameters were independently varied to determine the optimal parameter settings for monitoring several exemplary major constituents using the preferred voltammetric system of FIG. 1. It should be emphasized that while the parameter settings described in the examples below are optimal, the technique may produce useful results using parameters outside the specified optimal ranges. In applying other voltammetric techniques in accordance with the method of the present invention, a similar set of parameters applicable to that technique would have to be optimized. The set of applicable parameters may be estimated by reference to the manner in which the particular voltammetric technique has been applied to trace constituent detection.

In general, certain settings of the above physical test parameters are particularly well-suited for monitoring major constituent concentrations in accordance with the preferred embodiment of FIG. 1. The working electrode is preferably pretreated to remove contaminants at an anodic potential of about 1.5 to 3 volts, for a period of about 5 to 30 seconds. A sinusoidal ac waveform with an amplitude of about 20 to 30 mv root mean square (rms) and a frequency of about 50 to 2,000 Hz is superimposed on a dc signal which is swept between ±3 V which encompasses both stripping and plating electrode voltages. The DC sweep ranges depend on the specific baths. Optimal spectral peak resolution is obtained using the second harmonic of the ac response current, measured using a phase angle offset of about 0 to 45 degrees. Further improvements in monitoring accuracy are obtained by stirring the solution, and maintaining it at an optimum temperature range depending on each plating bath.

Examples of the optimization of the exemplary voltammetric system of FIG. 1 to the detection of specific major constituents are described below with reference to FIGS. 2–9. It should be noted that in FIGS. 2–9, the time scale and voltage settings were the same in all cases and are not specifically indicated in the figures. The important point is to compare the figures for the same plating bath solution with particular reference to the height of peak P, as described below.

One major constituent within an acid copper plating bath is sulfuric acid. Optimal ac current spectra of the type shown in FIGS. 2 and 3 were obtained for sulfuric acid concentrations in an acid copper bath using the following system parameters. Prior to each measurement, the working electrode was pretreated at an anodic potential of about 1.5 to 3 volts for a period of about 10 to 30 seconds. An ac signal of about 20 to 30 mv rms amplitude and about 50 to 1,500 Hz frequency was superimposed on a dc sweep signal. The dc signal was swept from about 0.4 to −0.5 volts and reversed to about 0.5 volts at a rate of about 20 to 500 mv/sec. The most sensitive spectral peak was found on the quadrature component of the ac response signal second harmonic, measured using a phase angle offset of about 0 to 45 degrees. During the measurement, the solution within the electrochemical cell was stirred continuously. The solution was maintained at a temperature of about 25° C.

Figure 2:
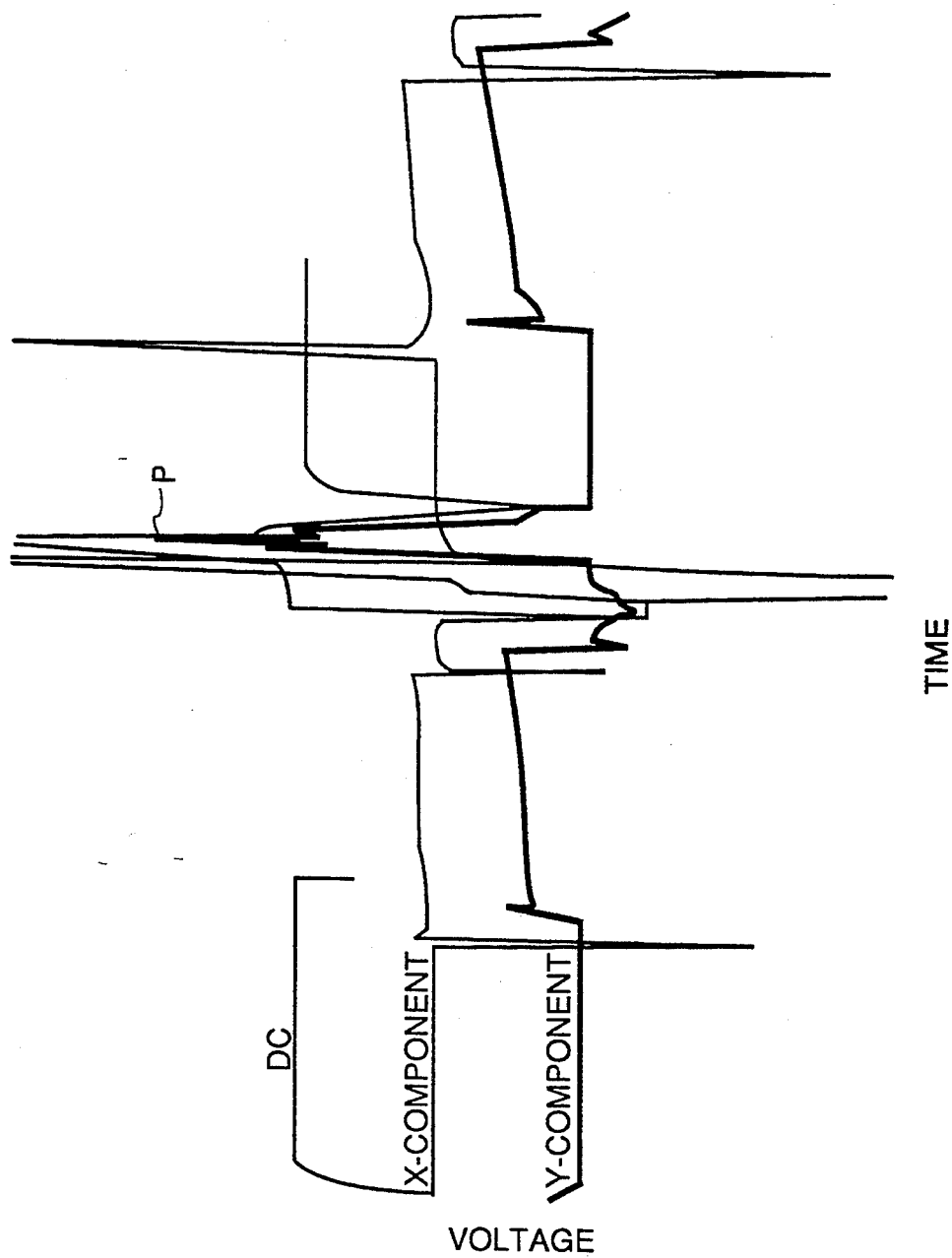
FIGS. 2-9 show exemplary ac current spectra obtained in accordance with the method of the present invention for exemplary plating baths with various types and concentrations of major constituents.
Figure 3:
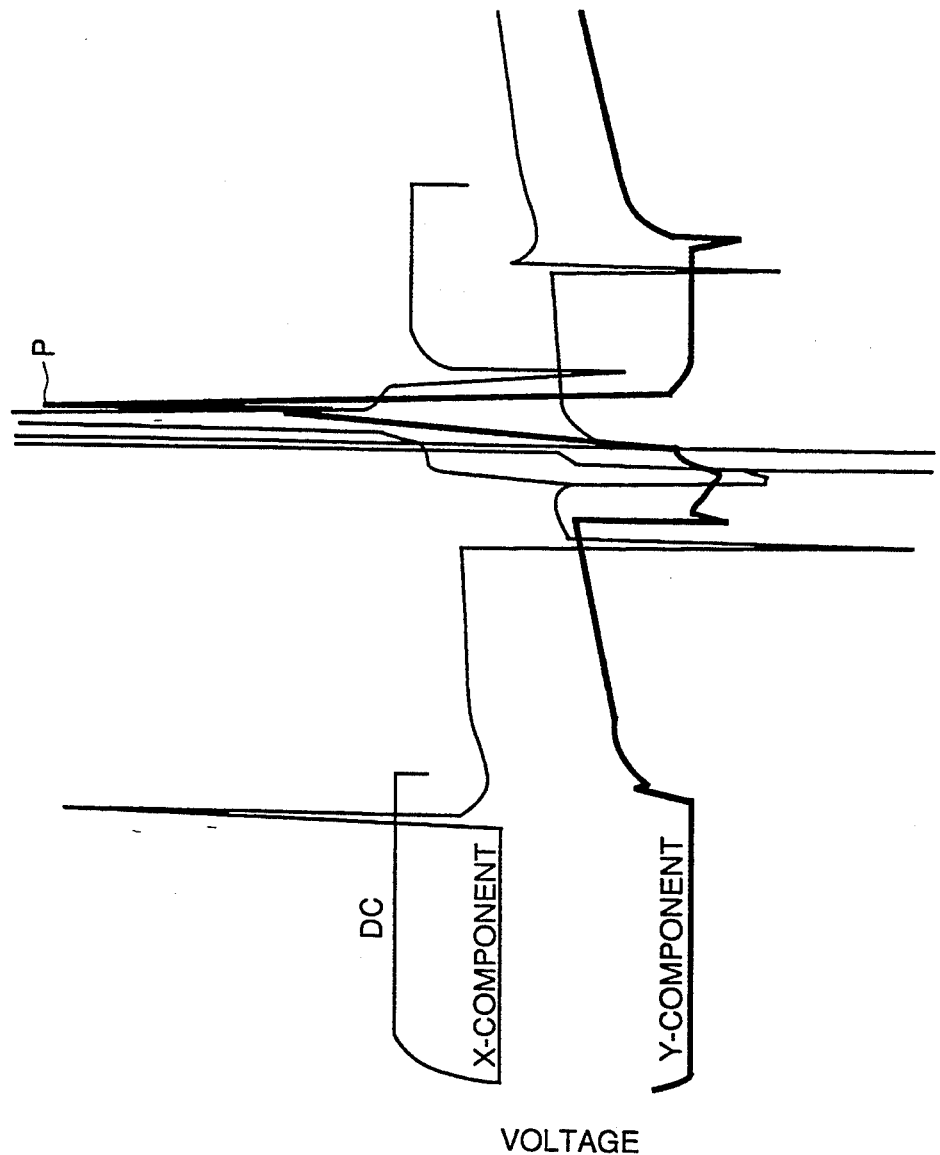

Referring now to FIG. 2, an acid copper plating solution containing 10 oz/gal copper sulfate, 20 oz/gal acid, 5 ml/liter carrier, 30 ppm chloride and 5 ml/liter brightener was analyzed using the above system parameters. The height of peak P measures about 652 mv relative to a copper reference electrode and corresponds to a concentration of 20 oz/gal of sulfuric acid within the plating bath solution. In FIG. 3 the effect of increasing the concentration of sulfuric acid within the solution of FIG. 2 to 30 oz/gal is shown. The resulting ac response peak P measured 870 mv, thus reflecting the increase in the sulfuric acid content of the solution. The method was applied to several other concentrations of sulfuric acid to verify repeatability. When using the above identified optimal parameters, the sensitivity of the detection of sulfuric acid concentration was about 22 to 30 mv/(oz/gal sulfuric acid). A one oz/gal change in the concentration of sulfuric acid in the solution would thus result in a change in the peak P voltage of about 22 to 30 mv.

In another example, optimal system parameters have been determined for detecting the concentration of chromic acid in an ATOCHEM HCR-840 chromium plating bath. An ac signal of about 20 mv to 30 mv rms amplitude and about 100 to 1,000 Hz frequency was superimposed on a dc sweep signal. The dc signal was swept from about 2.4 to $-1.5$ volts and reversed to about 2 volts at a rate of about 50 to 100 mv/sec. The most sensitive spectral peak was found on the quadrature component of the ac response signal second harmonic, measured at a phase angle offset of about 10 degrees. During the measurement, the solution within the electrochemical cell was stirred continuously. The solution was maintained at a temperature of about 60° C.

Figure 4:
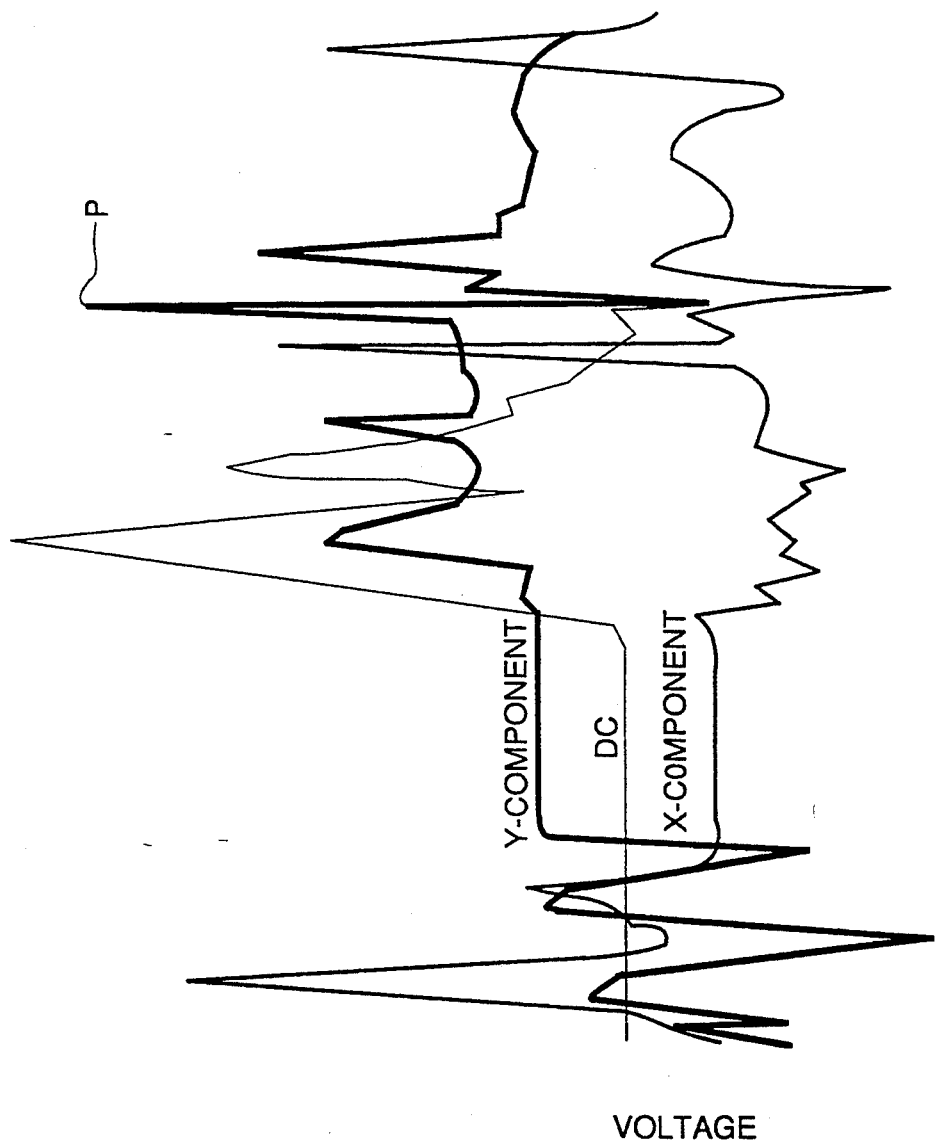
Figure 5:
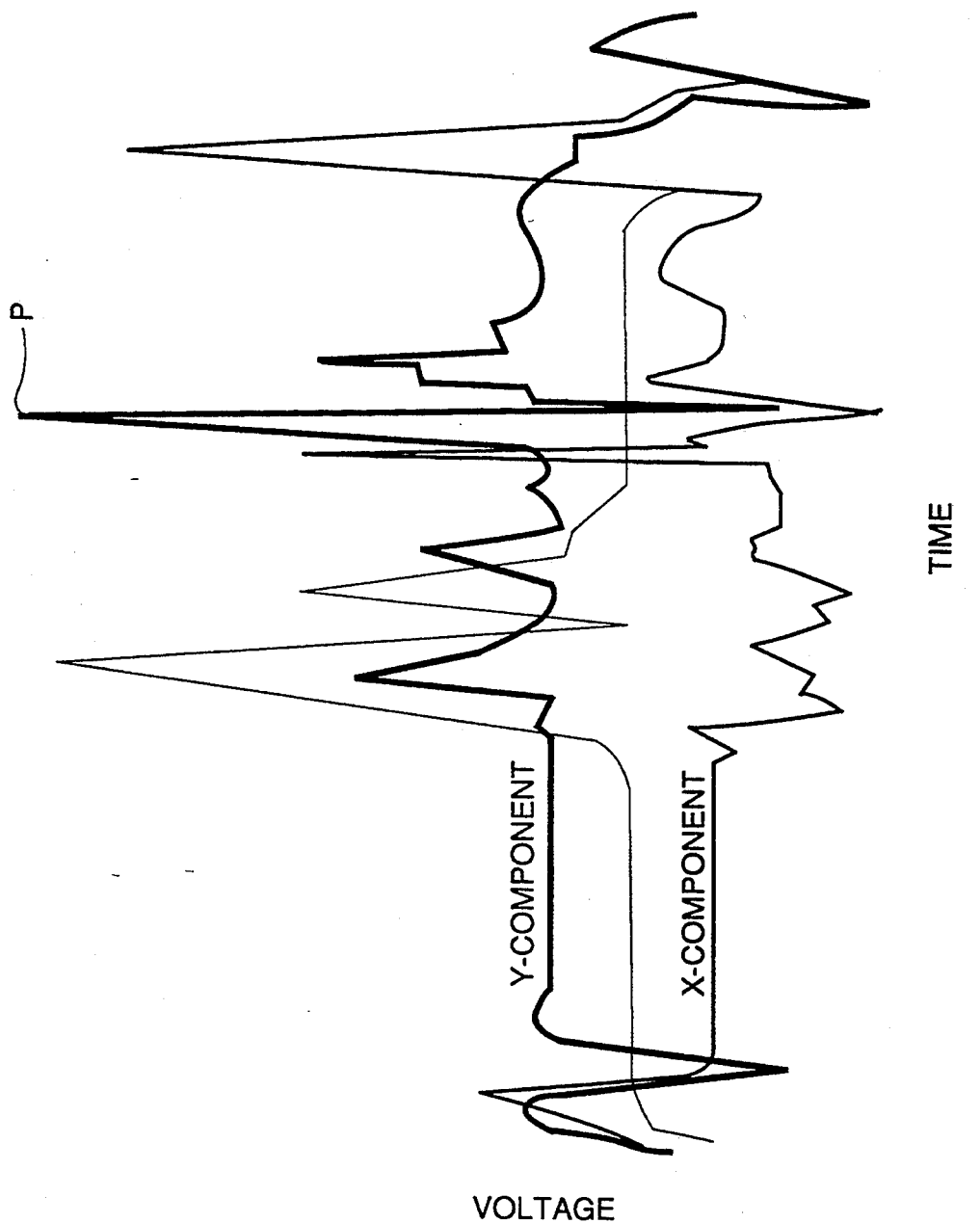

The spectra of FIG. 4 result from the application of a signal within the above optimal range to a solution containing 225 g/liter chromium trioxide, 1 g/liter sulfate catalyst, and 4 g/l silicofluoride catalyst. The resulting peak P of the quadrature component of the ac portion of the response signal measured 135 mv. The resulting peak is well-defined and appears in a portion of the spectrum where there is little other activity. The effect of increasing the chromic acid content of the solution of FIG. 4 to 275 g/liter of chromium trioxide, is shown in FIG. 5. The height of peak P increases to 180 mv. Applying the method to solutions with different concentrations of chromic acid produced consistent results. The sensitivity of this chromic acid detection method is thus about 0.9 to 1.0 mv/(g/liter of chromium trioxide).

In a further example, optimal system parameters have been determined for obtaining accurate ac current spectra indicating levels of the major constituent free potassium cyanide within a silver cyanide plating bath. An ac signal of about 20 to 30 mv rms amplitude and about 100 to 2,000 Hz frequency was superimposed on a dc sweep signal. The dc signal was swept from about 0 to $-1.6$ volts and reversed to about 0.5 volts at a rate of about 100 to 200 mv/sec. The most sensitive spectral peak was found on the in-phase component of the ac response signal second harmonic, measured at a phase angle offset of about 0 degrees. The solution was maintained at a temperature of about 24° to 26° C.

Figure 6:
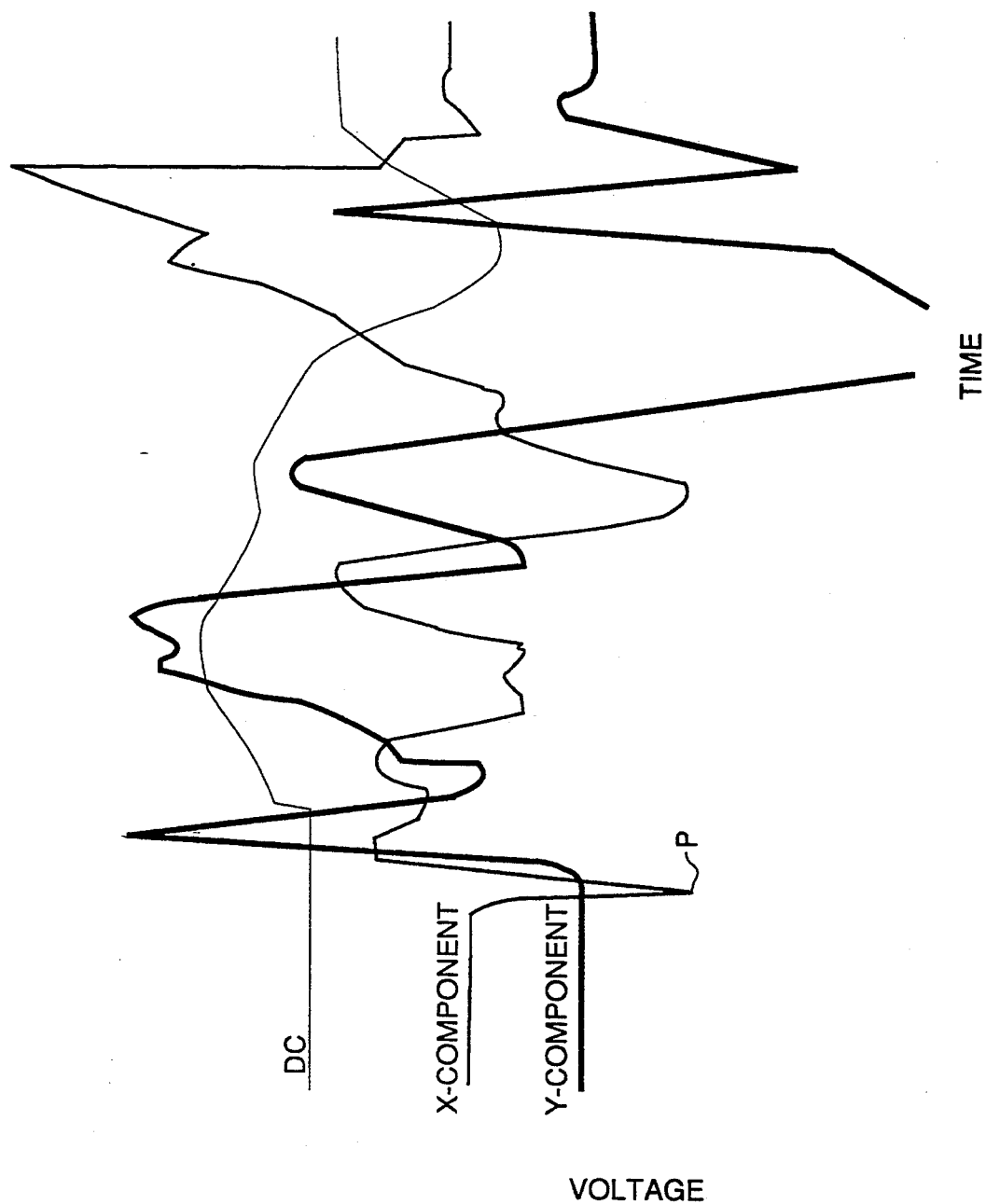
Figure 7:
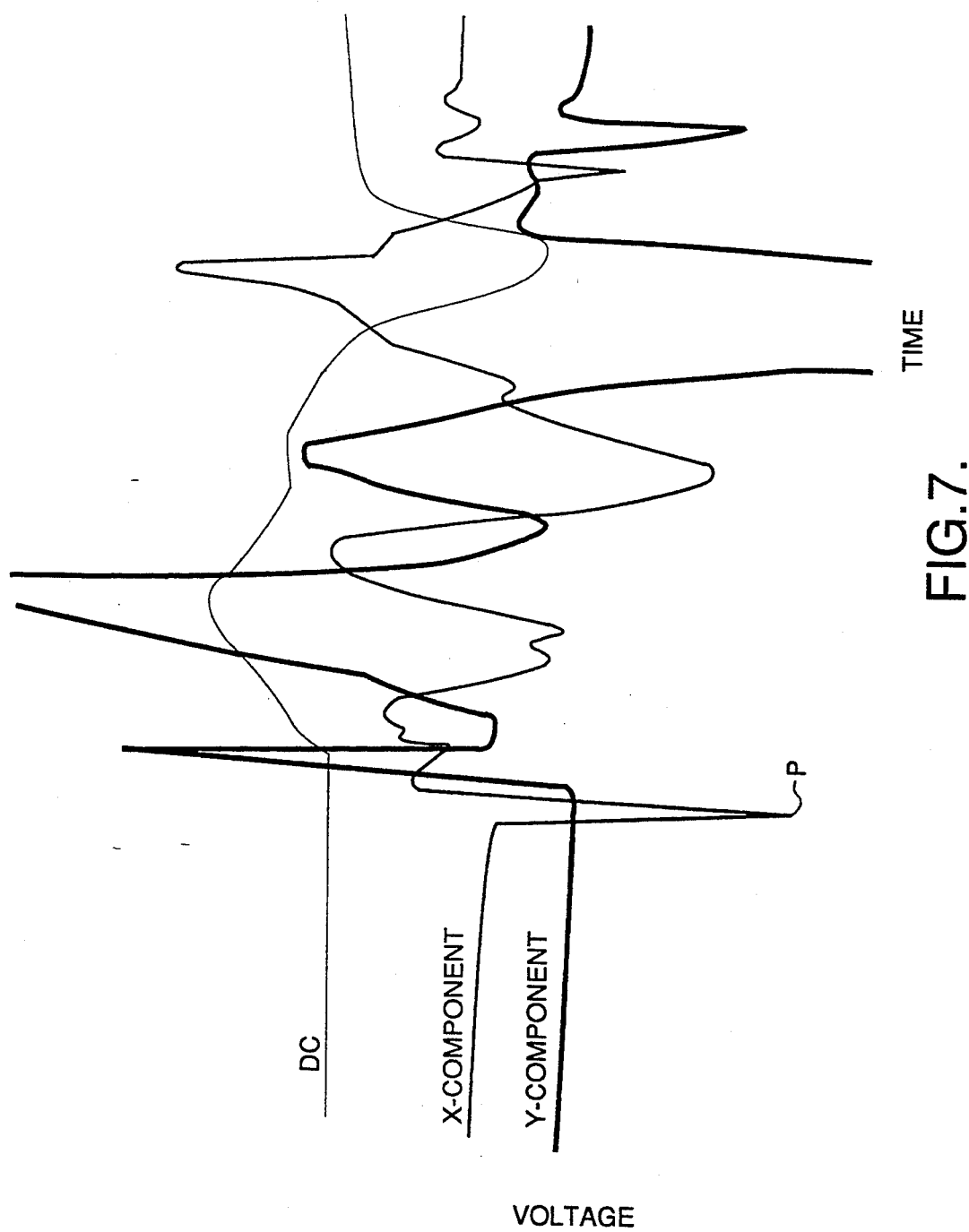

A signal within the above-specified optimal range was applied to a silver cyanide plating solution to produce the spectra of FIGS. 6 and 7. Initially, the solution contained 55 g/liter silver cyanide, 82.5 g/liter total KCN, 55 g/liter free potassium cyanide (82.5 g/liter total potassium cyanide), 150 g/liter $K_2CO_3$, 10 g/liter $K_2SO_4$, 0.1 ml/liter brightener, and had a pH of 12.3. The resultant spectra is shown in FIG. 6. The peak P of the in-phase component of the ac response signal appears at the onset of the plating portion of the dc swept signal and measures 75 mv. The effect of increasing the concentration of free potassium cyanide to 77.5 g/liter within the solution of FIG. 6 is seen in the spectra of FIG. 7. The height of peak P increased to 125 mv. Further measurements using other concentrations of free potassium cyanide yielded similar results. The sensitivity of this method as applied to the major constituent potassium cyanide within a silver cyanide plating bath is thus about 2 to 3 mv/(g/liter of free potassium cyanide).

Finally, the method of the present invention was applied to determine the concentration of potassium carbonate, a major constituent in a silver cyanide plating bath. An ac signal of about 20 to 30 mv rms amplitude and about 200 to 1,000 Hz frequency was superimposed on a dc sweep signal. The dc signal was swept from about 0 to $-1.5$ volts where it was held for 10 seconds and reversed to about 0.5 volts at a rate of about 100 to 200 mv/sec. The most sensitive spectral peak was found on the quadrature component of the ac response signal second harmonic, measured at a phase angle offset of about 0 to 24 degrees. The solution was maintained at a temperature of about 24° to 26° C.

Figure 8:
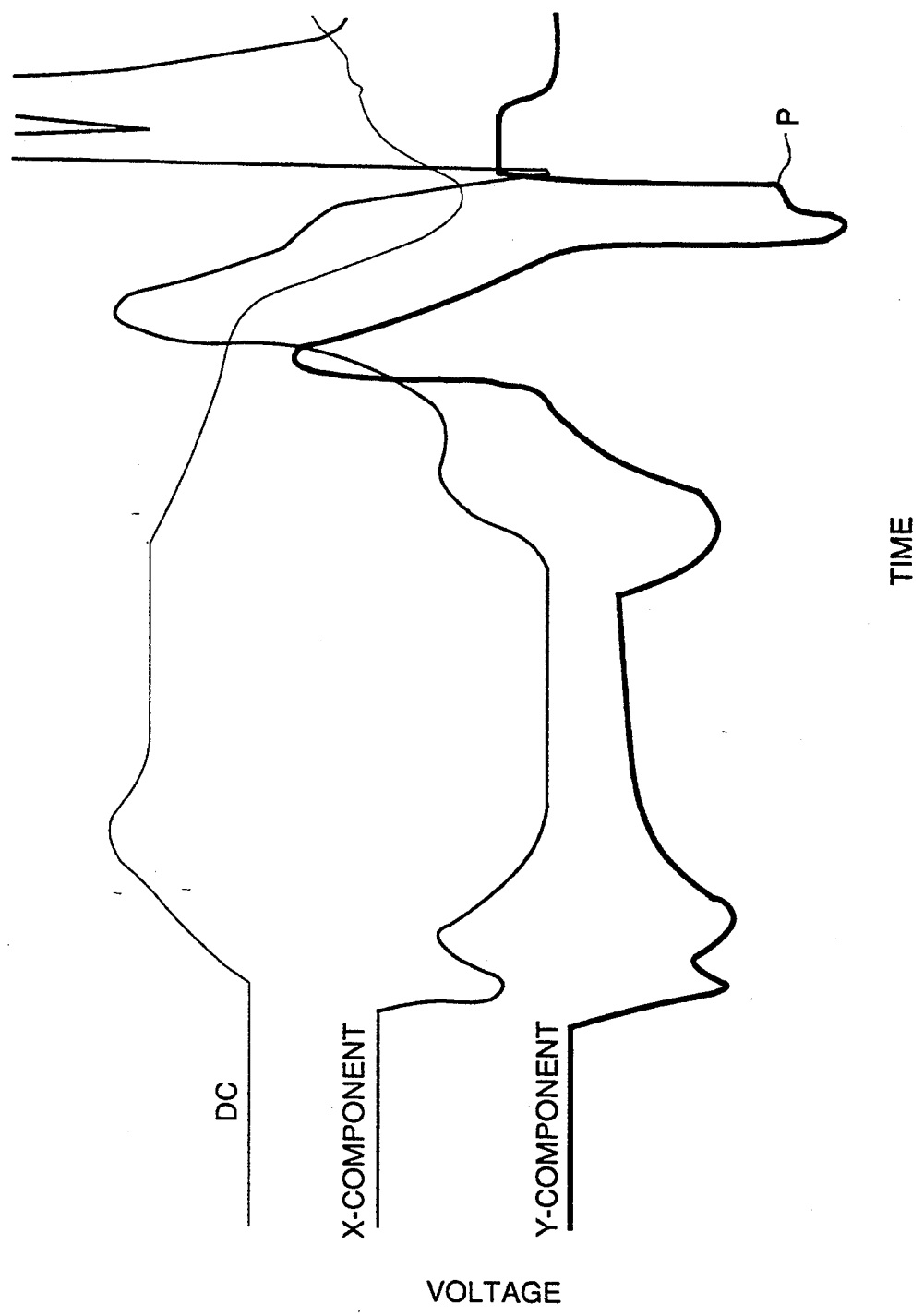
Figure 9:
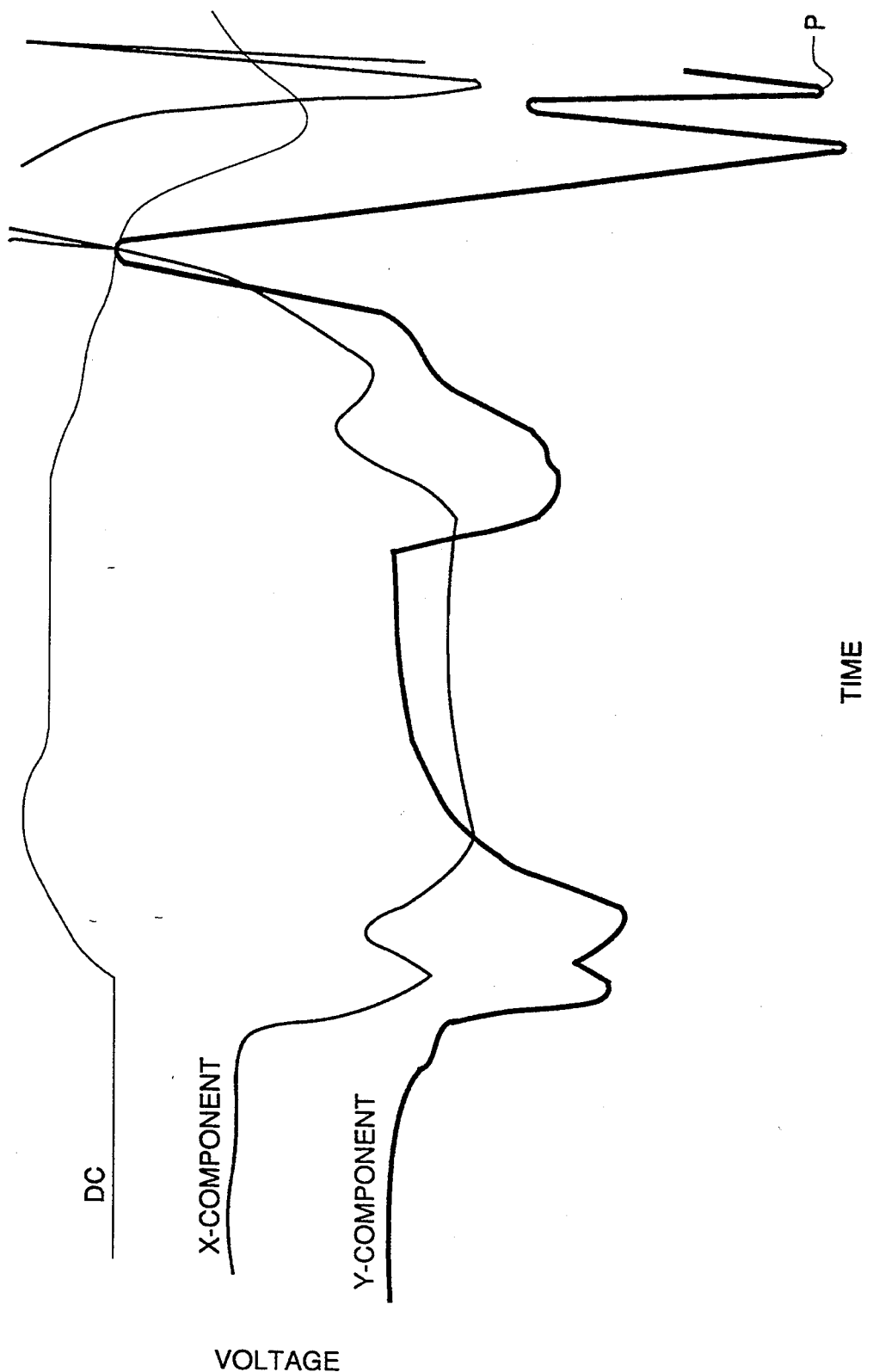

A signal within the range described above was applied to a silver cyanide plating solution containing 40 g/liter potassium carbonate, 55 g/liter AgCN, 82.5 g/liter total KCN, 10 g/liter $K_2SO_4$, and 0.1 ml/l brightener and having a pH of 12.5. The resulting spectra are shown in FIG. 8. The height of potassium carbonate diagnostic peak P measures 150 mv. The effect of increasing the concentration of potassium cyanide within the same solution to 180 g/liter results in the spectra of FIG. 9, where the diagnostic peak P shown measured 320 mv. The sensitivity of the method as applied to potassium carbonate within a silver cyanide plating bath is thus about 11 to 15 mv/(g/liter of potassium cyanide).

As can be seen in FIGS. 2 through 9, the method of the present invention produces reliable and repeatable spectra with easily distinguishable peaks corresponding to the concentration levels of various major constituents. These spectra can be used in conjunction with an overall plating bath analysis system which monitors and maintains proper levels of major constituents within various plating baths in real time without removing fluid from the plating tank.

Although the above description has been limited to analysis of exemplary plating bath major constituents using an exemplary ac voltammetry technique, this is by way of illustration and not limitation. It will be understood by those skilled in the art that many alternate implementations of this method are possible without deviating from the spirit and scope of the invention, which is limited only by the appended claims.

What is claimed is:

1. A method of monitoring the concentration of major constituents present in a plating bath solution, said method comprising the steps of:
    (a) applying a selected dc potential to a working electrode which has been subjected to pretreatment and is positioned within said solution wherein said dc potential has an amplitude range of about 2.4 to $-1.5$ volts and a sweep rate of about 20 to 1,000 mv/sec;
    (b) superimposing a constant ac signal on said dc potential applied to said working electrode, said ac signal having an amplitude of about 20 to 30 mv rms and a frequency of about 50 to 2,000 hertz and producing an ac current;
    (c) varying said dc potential at a chosen sweep rate over a chosen range;
    (d) measuring said ac current at one or more phase angles with respect to said constant ac signal between said working electrode and a counter electrode positioned within said solution as said dc potential is varied over said range, said measurement of ac current in relation to varying dc potential being expressed as an ac current spectra wherein each parameter comprising said amplitude of said ac signal, said frequency of said ac signal, said sweep rate of said dc potential, said range of said dc potential, said one or more phase angles, and said pretreatment of said working electrode is varied in combination, to determine the specific value of each said parameter which, when taken in combination with the remaining said parameters, provides maximum spectra detail in said ac current spectra to determine and monitor said major constituents in said solution which affect said plating deposit properties, wherein said major constituents constitute in excess of 5 percent of the total volume of said plating bath solution.

2. The method of claim 1 wherein measurement of said ac current is made at the second harmonic frequency relative to the frequency of said ac signal to further maximize said spectra detail.

3. The method of claim 1 wherein said plating bath is an acid copper plating bath and further wherein one of said monitored major constituents is sulfuric acid.

4. The method of claim 3 wherein said ac signal has an amplitude of about 20 to 30 mv rms and a frequency of about 50 to 1,500 hertz.

5. The method of claim 3 wherein said dc potential has an amplitude range of about 0.4 to −0.5 volts and a sweep rate of about 20 to 500 mv/sec.

6. The method of claim 1 wherein said plating bath is a chromium plating bath and further wherein one of said monitored major constituents is chromic acid.

7. The method of claim 6 wherein said ac signal has an amplitude of about 20 to 30 mv rms and a frequency of about 100 to 1,000 hertz.

8. The method of claim 6 wherein said dc potential has an amplitude range of about 2.4 to −1.5 volts and a sweep rate of about 50 to 100 mv/sec.

9. The method of claim 1 wherein said plating bath is a silver cyanide plating bath and further wherein one of said monitored major constituents is potassium cyanide.

10. The method of claim 9 wherein said ac signal has an amplitude of about 20 to 30 mv rms and a frequency of about 100 to 2,000 hertz.

11. The method of claim 9 wherein said dc potential has an amplitude range of about 0 to −1.6 volts and a sweep rate of about 100 to 200 mv/sec.

12. The method of claim 1 wherein said plating bath is a silver cyanide plating bath and further wherein one of said monitored major constituents is potassium carbonate.

13. The method of claim 12 wherein said ac signal has an amplitude of about 20 to 30 mv rms and a frequency of about 200 to 1,000 hertz.

14. The method of claim 12 wherein said dc potential has an amplitude range of about 0 to −1.5 volts which is held constant for 10 seconds and a sweep rate of about 100 to 200 mv/sec.

15. The method of claim 1 further comprising, prior to step (a), pretreating said working electrode to remove contaminants therefrom.

* * * * *